United States Patent
Nakagawa et al.

(10) Patent No.: US 6,709,632 B2
(45) Date of Patent: Mar. 23, 2004

(54) ICP ANALYZER

(75) Inventors: Yoshitomi Nakagawa, Chiba (JP); Yasuyuki Takagi, Chiba (JP)

(73) Assignee: SII NanoTechnology Inc., Chiba (JP)

(*) Notice: Subject to any disclaimer, the term of this patent is extended or adjusted under 35 U.S.C. 154(b) by 364 days.

(21) Appl. No.: 09/861,303

(22) Filed: May 18, 2001

(65) Prior Publication Data

US 2002/0001540 A1 Jan. 3, 2002

(51) Int. Cl.$^7$ ............................................. G01N 27/00
(52) U.S. Cl. ........................ 422/54; 436/153; 436/154; 250/288; 356/316
(58) Field of Search ................... 422/99, 54; 436/154, 436/153; 250/288; 356/316

(56) References Cited

U.S. PATENT DOCUMENTS

| | | | |
|---|---|---|---|
| 2,069,455 A | * 2/1937 | Massa | 239/338 |
| 3,533,558 A | * 10/1970 | Masters | 239/404 |
| 4,362,274 A | * 12/1982 | Davis | 239/419.3 |
| 4,482,246 A | * 11/1984 | Meyer et al. | 356/316 |
| 4,575,609 A | * 3/1986 | Fassel et al. | 219/121.59 |
| 4,990,740 A | * 2/1991 | Meyer | 219/121.52 |
| 5,066,125 A | * 11/1991 | Rogers et al. | 356/316 |
| 5,233,156 A | * 8/1993 | Chan et al. | 219/121.52 |
| 5,308,977 A | * 5/1994 | Oishi et al. | 250/288 |
| 5,477,048 A | * 12/1995 | Nakagawa et al. | 250/288 |
| 5,705,787 A | * 1/1998 | Karanassios | 219/121.52 |
| 5,925,266 A | * 7/1999 | Gagne | 219/121.48 |
| 5,939,648 A | * 8/1999 | Phan | 73/864.81 |
| 5,969,352 A | * 10/1999 | French et al. | 250/288 |

FOREIGN PATENT DOCUMENTS

| | | | | |
|---|---|---|---|---|
| JP | 08138619 A | * | 5/1996 | H01J/49/04 |
| WO | WO 9829896 A1 | * | 7/1998 | H01J/49/04 |

* cited by examiner

Primary Examiner—Arlen Soderquist
Assistant Examiner—Elizabeth Quan
(74) Attorney, Agent, or Firm—Adam & Wilks

(57) ABSTRACT

An ICP analyzer has a nebulizer for nebulizing a sample fluid for the purpose of analyzing microscopic impurities within the sample fluid, a plasma torch for introducing nebulized spray into a plasma, and a spray chamber disposed between the nebulizer and the plasma torch for separating spray comprised of microscopic particles from the nebulized spray prior to introduction thereof into the plasma torch. A heating section is provided at a central portion of the spray chamber and a cooling section is provided at a peripheral section of the spray chamber, and the spray is passed between the heating section and the cooling section to improve the efficiency sample introduction into the plasma to enable highly sensitive analysis by suppressing the proportion of a solvent component that reaches the plasma torch.

7 Claims, 5 Drawing Sheets

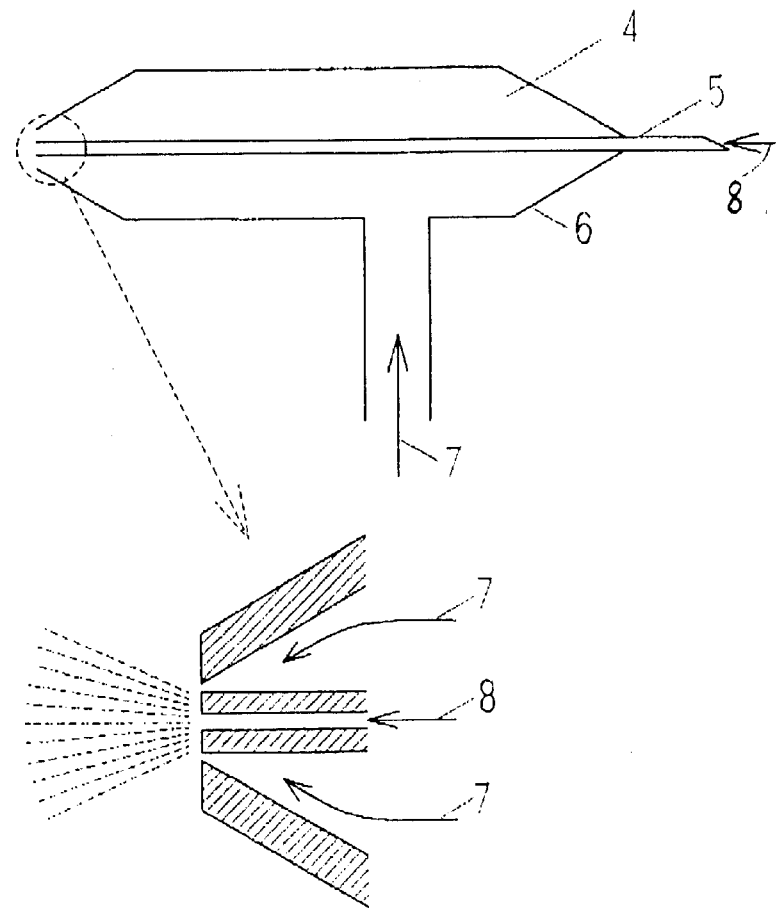
FIG. 4
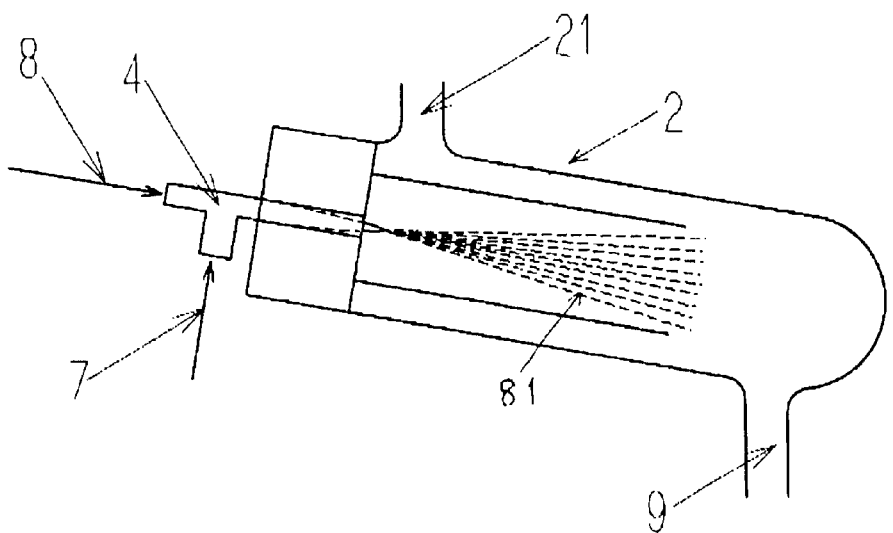
FIG. 5     PRIOR ART

ICP ANALYZER

BACKGROUND OF THE INVENTION

The present invention relates to a sample introduction section of an ICP analyzer for trace elements in a fluid.

FIG. 7 is a drawing showing the structure of an inductive plasma mass spectrometer of the related art. This device can be generally classified into a plasma emission section, an analyzing section, and a detecting section. Sample fluid 8 is turned into fine spray by a nebulizer 4 and introduced into a spray chamber 1. The spray chamber selects more minute spray particles of the sample 8 and guides them into a plasma torch 26. In the plasma torch 26, a high frequency is applied by a work coil 28 to gas supplied using a gas controller 27, to generate plasma. The sample 8 is introduced into this plasma and ionized. The ionized sample 8 is analyzed in the analyzer tube 31, and sent to a detector 32. Received information is converted into a signal in the detector 32, and sent to a data processing section 33 for quantitative and qualitative analysis.

A spray chamber of the related art, can be a Scott type having a double barrel (two tube) structure, as shown in FIG. 5, or a cyclon type, being barrel shaped, as shown in FIG. 6.

A general spray chamber, has a function of sorting only a sample 81 having a spray of small particles from the sample fluid 8 atomized by the nebulizer 4. As shown in FIG. 7, the finely misted sample 81 passes through a sample outlet pipe 21 and is introduced into the plasma torch 26.

The plasma torch 26 has the function of generating an argon plasma 30, and introducing the finely misted sample 81 into the argon plasma. The principle for generating argon plasma is to apply a high frequency from a high frequency power source 29 and work coil 28 using an inductive coupling method to argon gas introduced from a gas controller, and generate plasma by electrical discharge.

The nebulizer 4 has the function of atomizing the sample fluid 8. FIG. 4 is a structural diagram of the nebulizer 4, and it has a double barrel structure overall. A carrier gas 7 gushing from a gap between the inner tube 5 and the outer tube 6 of the double barrel structure sucks up the sample 8 inside the inner tube 5 and atomizes it.

The Scott type spray chamber 2 atomizes a sample 8 from the nebulizer 4 along an axis. Large spray particles collide with the walls of the spray chamber 2 due to their weight and inertia, and are ejected from a drain 9. Thus, only fine particles are introduced into the plasma torch 26.

The cyclon type spray chamber atomizes the sample 8 so that spray particles swirl. Spray of large particles collides with the inner walls and is expelled from the drain 9, so only spray of fine particles passes through the centrally inserted sample outlet pipe 21 and is introduced into the plasma inside the plasma torch 26.

With the spray chamber of the related art, it is necessary to efficiently expel portions of the atomized spray having large particles to the drain 9. The proportion of the sample 8 introduced into the plasma depends on the particle diameter distribution of the atomized particles, but there is a problem that in the case where a normal nebulizer 4 is used, this is as low as around 2%. Also, if the diameter and length of the spray chamber is changed to increase the proportion of the sample introduced, there is a problem in that the plasma becomes unstable, and the measurement accuracy decreases. In the worst case, it becomes impossible to maintain the plasma, and it is impossible to avoid interrupting measurement. Also, in the case of ICP-MS, interference attributable to the solvent increases. The analytical performance of particles subjected to the resultant interference therefore deteriorates slightly.

For example, argon constituting the plasma combines with oxygen in the solvent (usually water) to become argon oxide, and exerts an influence. Also, heavy rare earth elements are subject to the influence of light rare earth elements.

SUMMARY OF THE INVENTION

The present invention solves the above described problems, and an object of the present invention is to improve the efficiency of introducing a sample 8 into plasma without making the plasma unstable, suppress the influence on sample elements attributable to a solvent, and improve analysis performance.

With the present invention, in a spray chamber for separating particle diameters of the spray, spray particles of a sample from the nebulizer that have been atomized inside the spray chamber are heated and made smaller by heating of a central portion of the spray chamber. Also, the periphery of the spray chamber is cooled, and even if there is water vapor present a solvent component, inside the spray, this solvent component is condensed. Further, large diameter particles are caused to attach to the inner wall surface of the middle tube by causing the spray to swirl. With the present invention, the spray chamber has, for example, a triple tube structure comprising an inner tube, a middle tube and an outer tube, with the two ends of the inner tube being open, two end surfaces reaching from the inside of the inner tube to the middle tube and the outer tube being hermetically sealed. A heating member is fitted into the inner tube, a cooling layer is provided between the middle tube and the outer tube, and mist nebulized by the nebulizer is introduced between the inner tube and the middle tube, passed through, and ejected.

BRIEF DESCRIPTION OF THE DRAWINGS

FIG. 4 is a cross sectional diagram and an end magnification of a nebulizer.

FIG. 5 is a plan view of a Scott type spray chamber used in a conventional analyzer.

DETAILED DESCRIPTION OF THE PREFERRED EMBODIMENT

Figure 1:
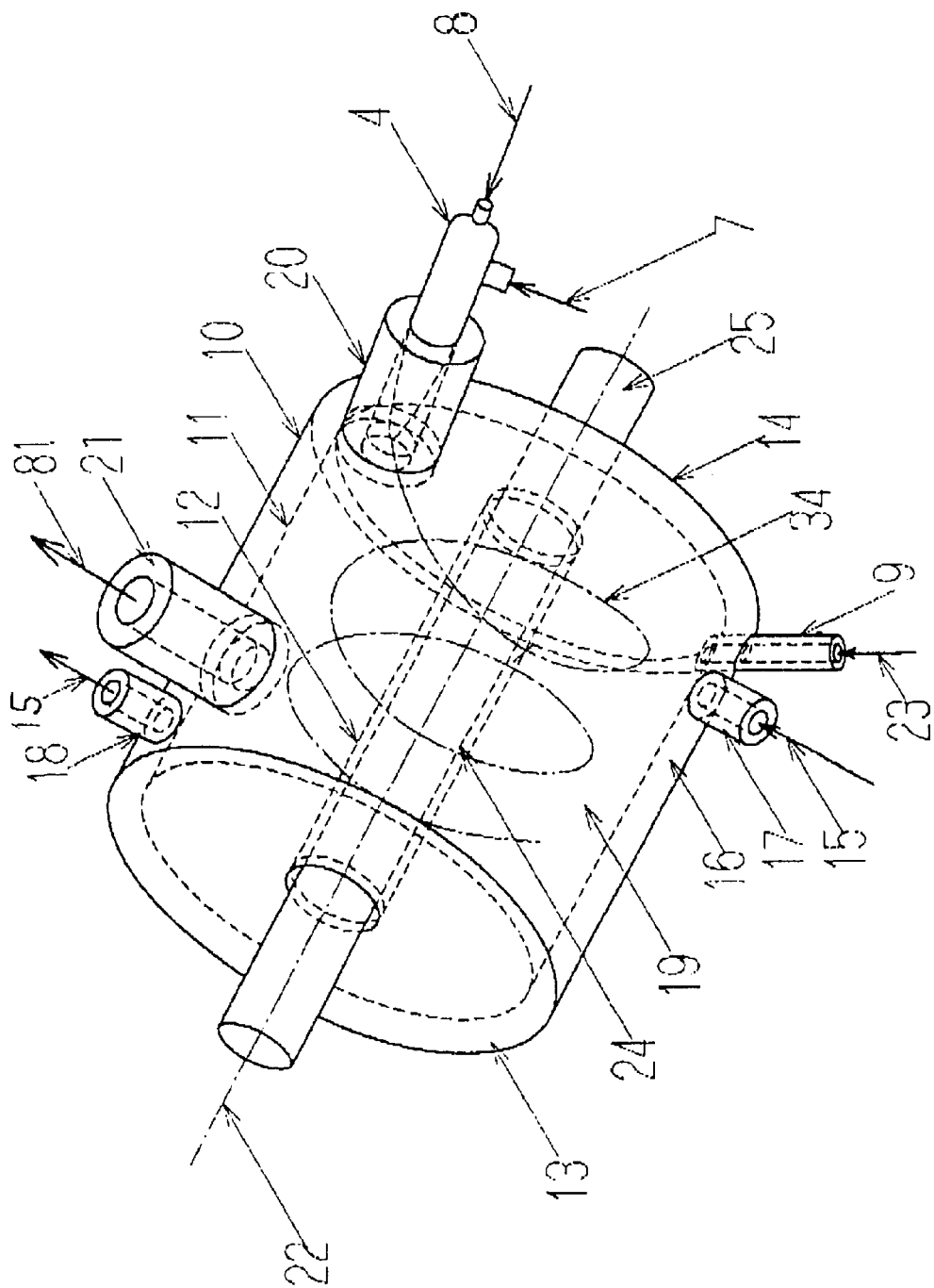
FIG. 1 is a perspective drawing of a spray chamber of an embodiment of the present invention.
Figure 2A:
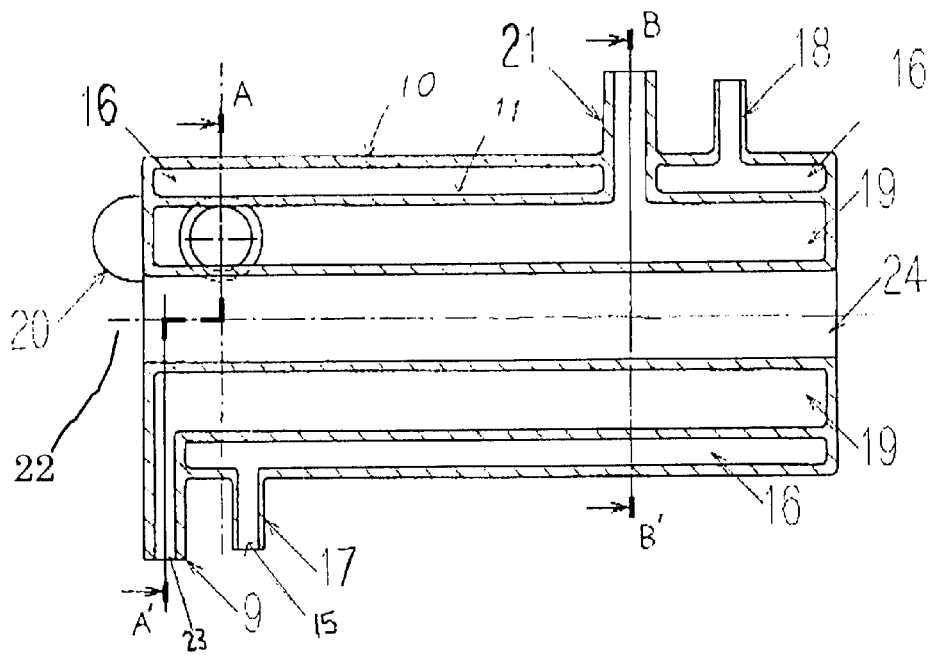
FIG. 2A is a cross sectional drawing of the spray chamber of the embodiment of the present invention.
Figure 2B:
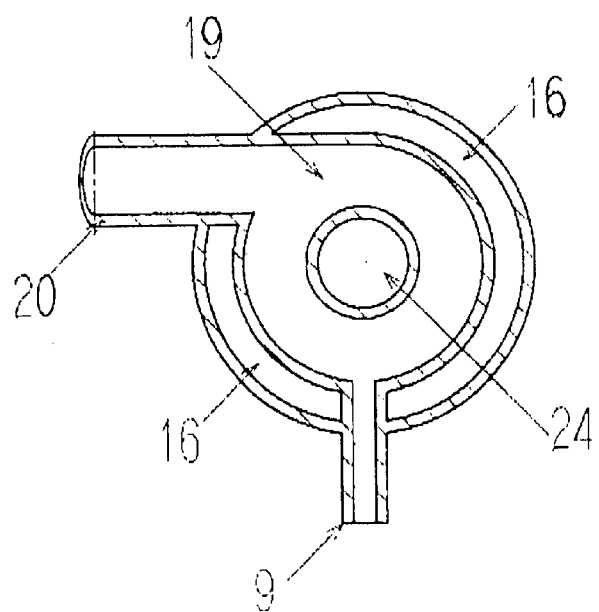
FIG. 2B is a cross section along line A–A' in FIG. 2A.
Figure 2C:
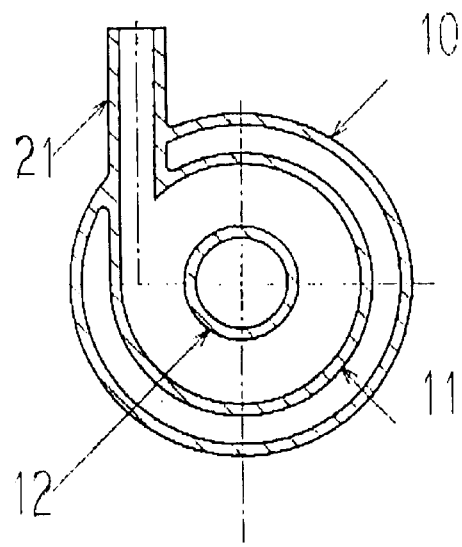
FIG. 2C is a cross section along line B–B' in FIG. 2A.

An embodiment of the present invention will be described in detail based on FIGS. 1, 2A, 2B, 2C and 3. The spray chamber of the present invention has a triple cylindrical pipe structure, as shown in FIGS. 2A, 2B, 2C. Each of the pipes constituting the triple piped structure will be called, from the outer side to the inner side, an outer tube 10, a middle tube 11 and an inner tube 12. Both ends of the spray chamber are blocked off by discs of the same diameter as the outer tube 10, at an upper end 13 and a lower end 14 having holes opening with the same diameter as a core tube.

A space between the outer tube 10 and the middle tube 11 acts as a cooling layer 16 for circulating coolant 15.

A coolant inlet pipe 17 and a coolant outlet pipe 18 jut out from a wall surface of the outer tube 10 in a direction normal to a central axis 22 of the cylinder. In order to cool the whole of the coolant layer 16, the coolant inlet pipe 17 is attached at a position lower than the coolant outlet pipe 18.

A space between the middle tube 11 and the inner tube 12 constitutes a spray layer 19 for allowing the discharged sample 8 to flow in from the nebulizer 4.

The inside of the spray layer 19 faces from the lower end surface to the upper end surface 13, and the sample introduction tube 20 for introducing the spiraling sample 8, and the sample outlet tube 21 connected to the torch, are attached as shown below.

As shown in FIGS. 2A, 2B, 2C, the attachment position of the sample introduction tube 20 and the sample outlet tube 21 is at a wall surface of the middle tube, with the sample introduction tube 20 being attached to the lower end surface 14 side and the sample outlet tube 21 being attached to the upper end surface 13 side. At this time, because the cooling layer is at the peripheral sections of the spray layer 19, the sample 8 and the coolant 15 are kept apart by the wall surfaces of the sample introduction tube 20 and the sample outlet tube 21.

Figure 3:
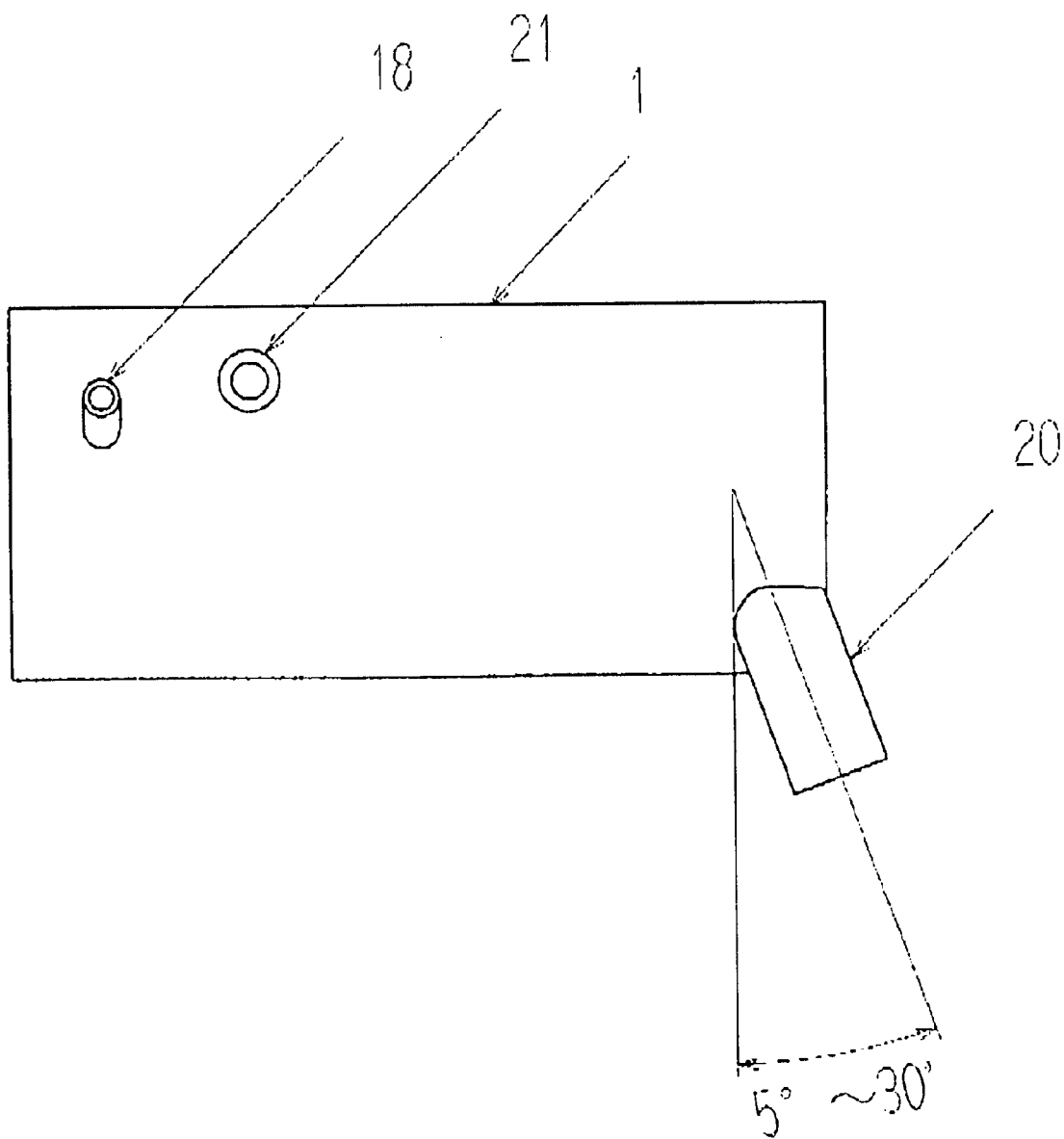
FIG. 3 is a top view of a spray chamber of the embodiment of the present invention.
Figure 6:
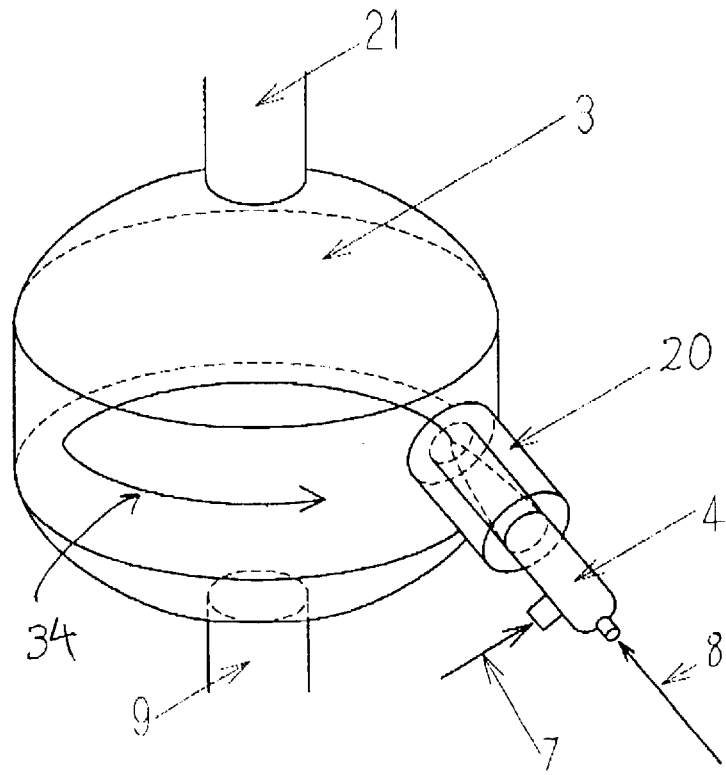
FIG. 6 is a perspective view of a cyclon type spray chamber used in a conventional analyzer.
Figure 7:
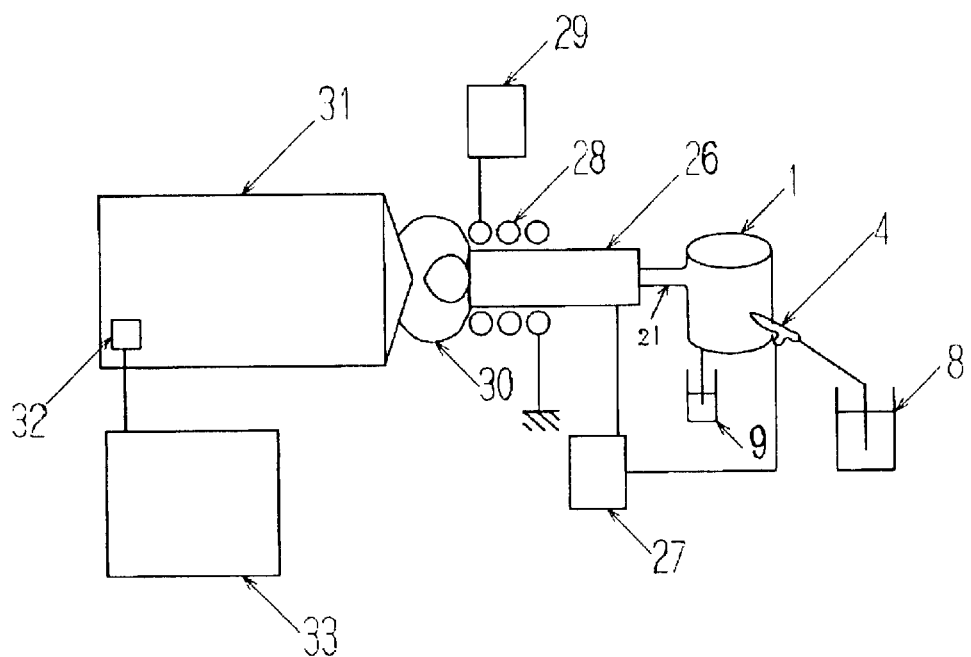
FIG. 7 is a structural drawing of an ICP analyzer of the present invention.

The attachment angle of the sample introduction tube 20 is 5–30 degrees with respect to a surface attached in a straight line of a vertical circle to a central axis 22 of the outer tube 10, as shown by the A—A cross section in FIGS. 2A, 2B, 2C, and also extending to the central axis 22, as shown in the top view of the spray chamber of FIG. 3.

The attachment angle of the sample outlet tube 21, similar to the attachment angle of the sample introduction tube 20, is parallel with respect to a surface attached in a straight line of a vertical circle to a central axis 22, as shown by the B—B cross section in FIGS. 2A, 2B, 2C, and extending to the central axis 22.

A drain tube 9 is attached for ejecting parts of the sample 8 that have condensed inside the spray layer 19. The drain tube 9 is also attached to the middle tube wall surface 11, and coolant 15 is kept away from the drainage water 23 by the wall surface of the tube such as the sample introduction tube 20 shown in FIGS. 2A, 2B.

The inside of the inner tube 12 at the central part of the spray chamber constitutes the heating layer 24. An infrared heater 25 is fitted into an inner section of the inner tube 12.

The spray chamber of the present invention is used being angled at 5–10° with the attached end of the drain pipe as a center. The reason for this is so as to efficiently discharge drainage from the drain pipe, and to cause coolant to circulate efficiently inside the coolant layer.

The spray chamber of the present invention brings about the following effects.

1) By warming a central portion of the spray chamber with the infra red heater 25 of the heating layer, the spray (sample 8) is heated and it is possible to make spray particles small, making it possible to increase the efficiency of introducing the sample into the plasma.

2) By causing the spray to swirl in a spiral manner, and using the cooling section to cool the peripheral surface of the spray chamber, spray of large particles is made to stick to the inner surface wall surface of the middle tube 11, and it is possible to condense excess solvent components to discharge them to the drain 9. Also, by doing this, it is possible to suppress the proportion of solvent components reaching the plasma torch 26, enabling high sensitivity analysis. This also enables stable analysis, and particularly makes it possible to control interference with ICP-MS.

3) by giving the spray chamber a triple-piped structure, the wall surfaces of the spray chamber are heated and cooled directly and it is possible to efficiently convey heat to the spray particles inside the spray layer. Also, by having both ends of the inner tube open and making the heating member detachable, it is made easy to replace the heating member.

What is claimed is:

1. An ICP analyzer comprising: a nebulizer for nebulizing a sample fluid to produce a nebulized mist of the sample fluid for the purpose of analyzing microscopic impurities within the sample fluid; a plasma torch for producing a plasma and introducing the nebulized mist into the plasma; and a spray chamber disposed between the nebulizer and the plasma torch for separating spray comprised of microscopic particles from the nebulized mist prior to introduction of the nebulized mist into the plasma, the spray chamber comprising a central portion having a heating section and an outer portion having a cooling section, the spray being passed between the heating section and the cooling section.

2. An ICP analyzer according to claim 1; wherein the spray chamber has a triple tube structure comprising an inner tube, a middle tube and an outer tube, the inner tube having opposed open ends, the middle and outer tubes having opposed hermetically sealed ends; the heating section comprises a heating member fitted into the inner tube, and the cooling section comprises a cooling layer provided between the middle tube and the outer tube; and spray nebulized by the nebulizer is introduced between the inner tube and the middle tube, passed through and ejected.

3. An ICP analyzer according to claim 1; wherein the heating section comprises is an infra red heater.

4. A plasma analysis apparatus comprising: a sample vessel for containing a nebulized mist of a sample; a plasma torch for producing a plasma in the sample vessel; and a spray chamber for separating microscopic particles from the nebulized mist prior to introduction thereof into the sample vessel, the spray chamber comprising a central portion having a heating section and an outer portion having a cooling section, the nebulized mist being passed between the heating section and the cooling section.

5. A plasma analysis apparatus according to claim 4; wherein the spray chamber has a triple tube structure comprising an inner tube, a middle tube and an outer tube, the inner tube having opposed open ends, the middle and outer tubes having opposed hermetically sealed ends; the heating section comprises a heater fitted into the inner tube, and the cooling section comprises a cooling layer provided between the middle tube and the outer tube; and the nebulized mist is introduced between the inner tube and the middle tube, passed through and ejected.

6. A plasma analysis apparatus according to claim 4; wherein the heating section comprises an infra red heater.

7. A plasma analysis apparatus according to claim 4; wherein the spray chamber has a tubular configuration and a sample introduction port of the spray chamber is attached so that the nebulized spray swirls in a spiral manner, and is oriented at an angle within the range of 5° to 30° with respect to an axial direction of the tubular spray chamber.

* * * * *